United States Patent
Kodama et al.

(10) Patent No.: US 7,214,196 B2
(45) Date of Patent: May 8, 2007

(54) APPARATUS FOR MEASUREMENT OF WOMAN'S BODY

(75) Inventors: Miyuki Kodama, Tokyo (JP); Tomoko Takehara, Tokyo (JP)

(73) Assignee: Tanita Corporation, Tokyo (JP)

( * ) Notice: Subject to any disclaimer, the term of this patent is extended or adjusted under 35 U.S.C. 154(b) by 837 days.

(21) Appl. No.: 10/192,527

(22) Filed: Jul. 11, 2002

(65) Prior Publication Data

US 2003/0013988 A1  Jan. 16, 2003

(30) Foreign Application Priority Data

Jul. 13, 2001 (JP) ............................. 2001-213636
Apr. 5, 2002 (JP) ............................. 2002-103696

(51) Int. Cl.
*A61B 10/00* (2006.01)

(52) U.S. Cl. .................................... 600/551

(58) Field of Classification Search ................ 600/551, 600/550, 547, 587, 485, 500, 300
See application file for complete search history.

(56) References Cited

U.S. PATENT DOCUMENTS

| | | | |
|---|---|---|---|
| 4,125,111 A * | 11/1978 | Hudspeth et al. | 600/502 |
| 6,327,495 B1 * | 12/2001 | Iwabuchi et al. | 600/547 |
| 6,402,699 B1 * | 6/2002 | Kodama et al. | 600/551 |
| 6,403,380 B1 | 6/2002 | Catt et al. | |
| 2001/0053883 A1 * | 12/2001 | Yoshimura et al. | 600/587 |
| 2003/0120173 A1 * | 6/2003 | Saini et al. | 600/551 |

FOREIGN PATENT DOCUMENTS

| | | |
|---|---|---|
| CN | 1255321 A | 6/2000 |
| CN | 1292248 A | 4/2001 |
| EP | 1 084 676 | 3/2001 |
| EP | 1 084 676 A1 | 3/2001 |
| JP | 08-000583 | 1/1996 |
| JP | 11-088546 | 3/1999 |
| JP | 2001-231758 | 8/2001 |
| KR | 1998-023947 | 7/1998 |

OTHER PUBLICATIONS

Lamprecht, Virginia, M., et al. "Development of New Formulas to Identify the Fertile Time of the Menstrual Cycle." Contraception, vol. 54, 1996, ISSN: 0010-7824, pp. 339-343.

(Continued)

*Primary Examiner*—Max F. Hindenburg
*Assistant Examiner*—Brian Szmal
(74) *Attorney, Agent, or Firm*—McDermott Will & Emery LLP

(57) ABSTRACT

An apparatus is provided for measurement of a woman's body. Embodiments include an apparatus having a body parameter input unit, a menstruation date input unit, and a physical condition phase estimation unit for estimating the phase of physical condition of the person under test for a measurement day based on formulas for estimation of phase of body condition. After determining a change in an input body parameter, a display unit displays advice for the person under test for the measurement day, based on the change in body parameter and the phase of physical condition of the person for the measurement day estimated by the physical condition phase estimation unit.

12 Claims, 21 Drawing Sheets

OTHER PUBLICATIONS

Palmero F et al.: "Resting Heart rate HR in Women With and Without Premenstrual Symptoms PMS" Journal of Behavioral Medicine, vol. 14, No. 2, 1991, pp. 125-140, XP008009730 ISSN: 0160-7715 *p. 132, line 1-4*.

Dunne F P et al.: "Changes in Blood Pressure During the Normal Menstrual Cycle" Clinical Science (London), vol. 81, No. 4, 1991, pp. 515-518, XP008009731 ISSN: 0143-5221 *p. 515, section "Summary" *.

* cited by examiner

FIG.7

<Example of Main Physical Variation Occurred with Days since Menstruation (28-day period)>

| Technical Terms | Menstruation Phase | | | | Follicular Phase | | | | | | | Before and After Ovulation | | | | | Luteal Phase | | | | | | | | | | | |
|---|---|---|---|---|---|---|---|---|---|---|---|---|---|---|---|---|---|---|---|---|---|---|---|---|---|---|---|
| Terms Marked on Measuring Unit / Days | ①Menstruation Phase | | | | ②Diet Phase | | | | | | | ③Before-and-After Ovulation Phase | | | | | ④PMS Prevention Phase | | | | | ⑤PMS Phase | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| Basal Metabolism | →Decrease with Start of Menstruation | | | | Stable at Lower Level→→→→Tend to Gradually Increase | | | | | | | Slightly Increase →Increase after Ovulation | | | | | Higher Level | | | | | Higher Level | | | | | | |
| Change in Physical Condition / Condition | ・Pay attention to cold or anemia; ・Poor circulation of blood; ・Stomachache; ・Stiffness of shoulder or headache; ・Relieving constipation or suffering from diarrhea; ・Gradually restoring in latter half interval. | | | | ・Swelling gone down; ・physically lightened for becoming activity; ・Rapid recovery in physical power; ・Good chance for diet; ・Skin and hair in good condition; ・Mentally stable. | | | | | | | ・Changed in physical condition before and after ovulation (Changed in physical condition after ovulation: gradually becoming poor condition or swelling appeared) | | | | | | | | | | ・Heavy swelling appeared (tending to increase in body weight) ; ・Headache or stomachache; ・Feel lassitude or sleepy ・Irritation: desire to have a food containing much salt or sugar; ・Increase of appetite (Diet should be avoided); ●Others: various physically and mentally uncomfortable conditions. | | | | | | |

Do exercise without any strain →  Do exercise without any strain →

FIG.8

<Estimation of length of each phase in case where menstruation period is divided into five phases>

(1) Menstruation Phase = 1~a (2) Diet Phase    = (a+1)~{Average number of days during the period
    (Follicular Phase)    -(14+b)}
    ;or
    = (a+1)~{Minimum number of days during the period
    -(14+b)}

(3) Before-and-After    = {Average number of days during the period-(14+b-1)-2}
    Ovulation Phase    ~{Average number of days during the period-(14+b-1)+2}
    (Ovulation Phase)    ;or
    = {Minimum number of days during the period-(14+b-1)}
    ~{Minimum number of days during the period-(14+b-1)}
    ;or
    = {Maximum number of days during the period-(14+b-1)}
    ~{Maximum number of days during the period-(14+b-1)}

(4) PMS Prevention    = {Average number of days during the period-(14+b-1)+
    Phase    2+1}~{Average number of days during the period-(7+c)}
    (First Half of    ;or
    Luteal Phase)    = {Minimum number of days during the period-(14+b-1)
    +1}~{Minimum number of days during the period-(7+c)}
    ;or
    = {Maximum number of days during the period-(14+b-1)
    +1}~{Minimum number of days during the period-(7+c)}

(5) PMS Phase    = {Average number of days during the period-(7+c)+1}
    (Latter Half of    ~{Next menstruation input date-1}
    Luteal Phase)    ;or
    = {Minimum number of days during the period-(7+c)+1}
    ~{Next menstruation input date-1}

Notes: "a" means the length of menstruation phase, typically four days;
"b" means an adjustment interval for before-and-after ovulation phase, typically three days; and
"c" means an adjustment interval for PMS phase, typically 0 day.

FIG.9

| | ①Menstruation Phase | ②Diet Phase | ③Before-and-After Ovulation Phase | ④PMS Prevention Phase | ⑤PMS Phase |
|---|---|---|---|---|---|
| Increase in Percent fat ↑ | Advise to do light stretch for increasing metabolism while relaxing; and Advise about proper action and suitable nutrition for relieving menstruation pain. | Advise to do slightly hard aerobics; Advise about meal likely to provide weight reduction; and Instruct to correct one's behavior. | Watch with a jealous eye! Advise about action not to increase body weight, suitable aerobics, and proper nutrition for restoration from fatigue. | Advise to do ligth aerobics and to take meal for reducing swelling; and Prepare in an easy atate for PMS phase. | Advise about mael for eliminating or at least relieving swelling; and Make comfortable to eliminate irritation. |
| No change in Percent fat → (within ±0.5%) | Make it easy yourself; Advise about breathing method for increasing metabolism and improving circulation of blood; and Advise about proper action for relieving menstruation pain. | Advise to do aerobics for efficiently reducing body weight; and Advise about meal suitable for providing diet dffect. | Gradually become difficult to be lean,but make comfortable; Advise to do light aerobics for longer period of time; and Advise about proper nutrition for restoration from fatigue. | Advise to do exercise for eliminating any irritation and to take meal for preparation for PMS phase; and Advise about a water intake not to produce swelling in latter time. | Advise about meal and proper action for prevention of swelling; Advise to do exercise for eliminating any irritation; and Advise to live in an easy state. |
| Decrease in Percent fat ↓ | Take a rest; and Advise to have massage, to do exercise and to take meal for relieving menstruation pain. | Swelling is eliminated and body weight is reduced; and Advise to do exercise for tightening, with some muscle training as the central item to maintain the condition. | Advise to do exercise for tightening to maintain the body shape; and The physical condition is gradually becoming poor, so pay attention. | Advise to do exercise for making relax, and Advise about meal for adjusting physical condition for preparation for PMS phase. | Advise about proper action and nutrition for relaxing, and Advise mentally not to have any excessive effort. |

April 19, 2001

Body Weight: 45.1Kg

Percent Fat : 22.3%

M  25th day / 28 days

In PMS Phase

FIG.11
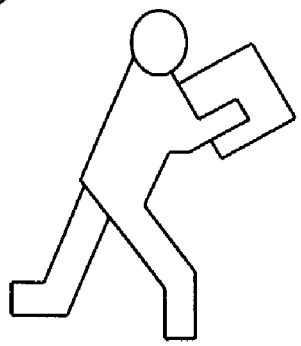
Take a rest leisurely without any strain because you are likely to feel tired in this phase.
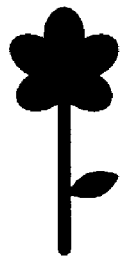
Vitamin B,C for roughness of skin
Calcium and magnesium for irritation
Deep breathing when irritated
Food recommended:
Fermented soybeans, spinach, banana

FIG.12
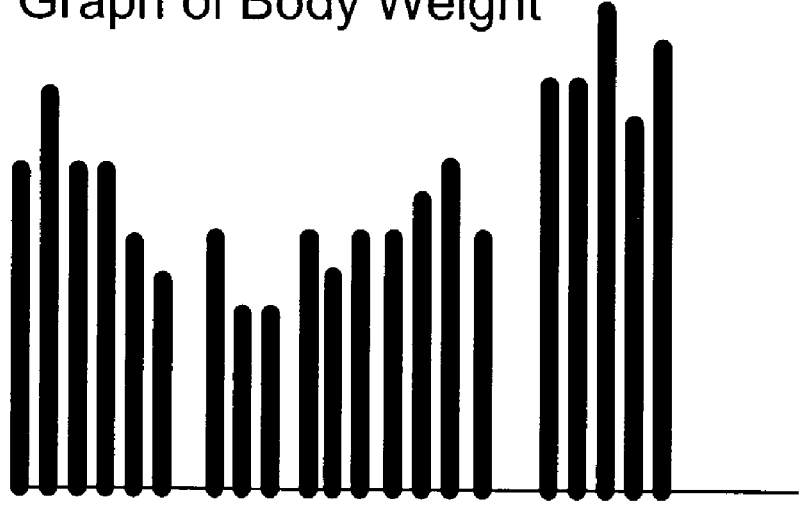
April 19, 2001
Graph of Body Weight
M  25th day / 28 days

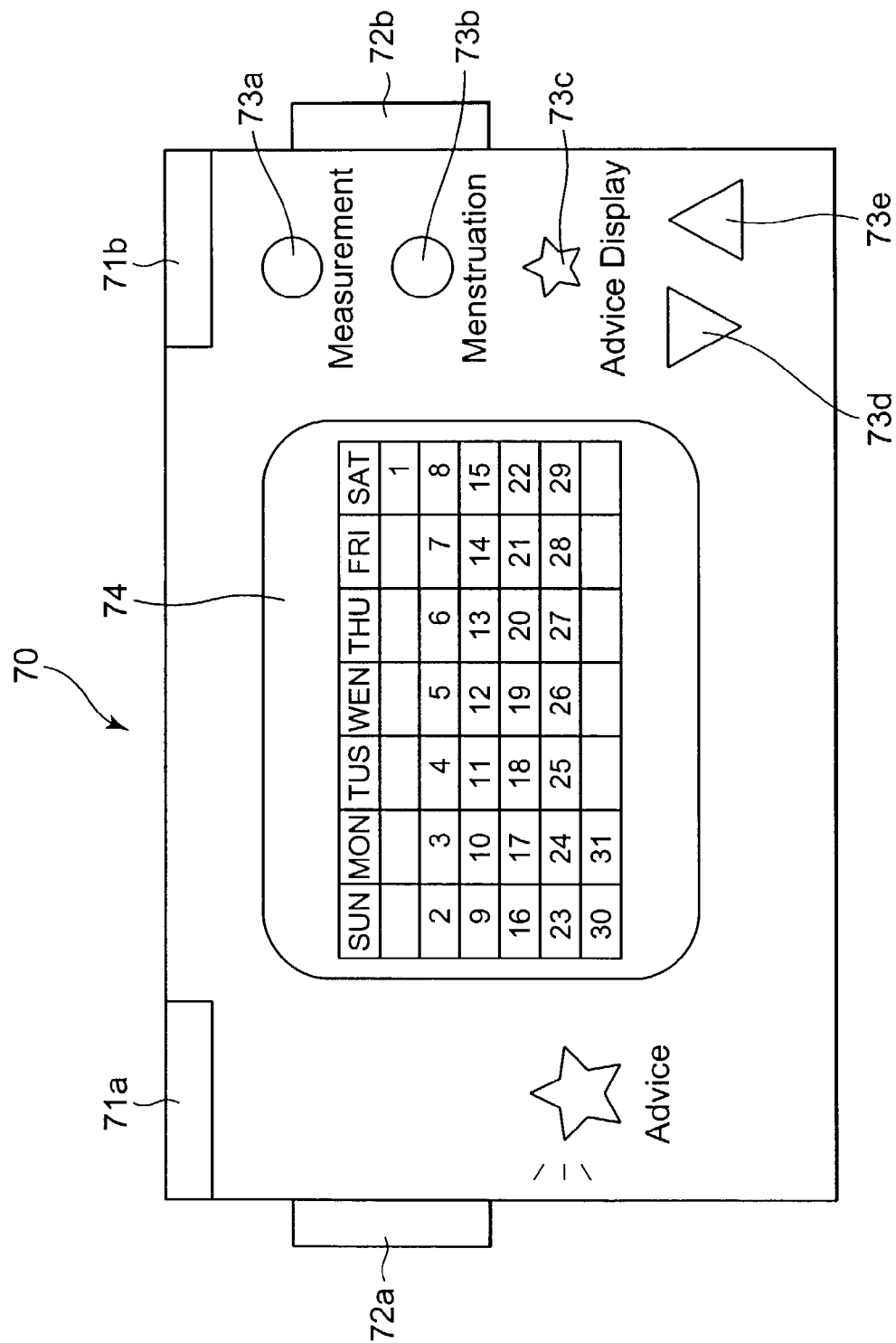

FIG.19

<Estimation of length of each phase in case where menstruation period is divided into four phases>

(1) Menstruation Phase = 1 ~ a (2) Diet Phase
(Follicular Phase)
= (a+1) ~ {Average number of days during the period -(14+b)+2} ;or
= (a+1) ~ {Minimum number of days during the period -(14+b)}

(3) PMS Prevention Phase
(First Half of Luteal Phase)
= {Average number of days during the period -(14+b-1)+2+1}
~ {Average number of days during the period -(7+c)} ;or
= {Minimum number of days during the period -(14+b-1)+1}
~ {Minimum number of days during the period -(7+c)} ;or
= {Maximum number of days during the period -(14+b-1)+1}
~ {minimum number of days during the period -(7+c)}

(4) PMS Phase
(Latter Half of Luteal Phase)
= {Average number of days during the period -(7+c)+1}
~ {Next menstruation input date-1}
;or
= {Minimum number of days during the period -(7+c)+1}
~ {Next menstruation input date-1}

Notes: "a" means the length of menstruation phase, typically four days;
"b" means an adjustment interval for ovulation day, typically 0 day;and
"c" means an adjustment interval for PMS phase, typically 0 day.

FIG.20

<Estimation of length of each phase in case where menstruation period is divided into three phases>

(1) Menstruation Phase = 1 ~ a (2) Diet Phase　　　　= (a+1) ~ {Average number of days during the
　　(Follicular Phase)　　period -(14+b)+2}
　　　　　　　　　　　　;or
　　　　　　　　　　　　= (a+1) ~ {Minimum number of days during the
　　　　　　　　　　　　period -(14+b)}

(3) PMS Phase　　　　= {Average number of days during the period
　　(Luteal Phase)　　　-(14+b)+2+1}
　　　　　　　　　　　　~ {Next menstruation input date -1}
　　　　　　　　　　　　;or
　　　　　　　　　　　　= {Minimum number of days during the period
　　　　　　　　　　　　-(14+b)+1}
　　　　　　　　　　　　~ {Next menstruation input date -1}

Notes: "a" means the length of menstruation phase, typically four days; and
"b" means an adjustment interval for ovulation day, typically 0 day.

FIG. 21

| | ① Menstruation Phase | ② Diet Phase | ③ Before-and-After Ovulation Phase | ④ PMS Prevention Phase | ⑤ PMS Phase |
|---|---|---|---|---|---|
| Increase in blood pressure (pulsation) ↑ | After menstruation the blood pressure(pulsation) will be decreased, but pay attention not to further increase. Save salt as much as possible and keep quiet. When suffering from heavy heabache or stomachache, take a rest without any strain. | Any increase in blood pressure(pulsation), if any, in this phase may be a symptom of any disease. Pay attention to save salt. If you feel poor physical condition go to see a doctor for advice. | Give a comment that there may cause big change in physical condition in this phase, and advise to save salt and to adjust the physical condition. | Because of possibility that the blood pressure (pulsation) is further increased after entering PMS phase, pay attention to save salt, to take a lot of vegetable and to adjust the physical condition in advance. | In this phase the blood pressure(pulsation) is likely to be increased, so save salt as much as possible and keep quiet. When suffering from heavy headache or stomachache, take a rest without any strain. (Give an advice about a meal for prevention of swelling.) |
| No change in blood pressure (pulsation) → | Make it easy on yourself; Advise to have massage for relieving menstruation pain; and Advise about breathing method for improving circulation of blood. | There is no problem. Advise to do exercise positively. | There is no problem. Advise to do exercise positively, while paying attention to any change in physical condition. | Advise to do exercise for eliminating any stress. Advise about water and salt intake not to produce any swelling. | Advise about proper meal and action to prevent any swelling; Advise to do exercise for eliminating any stress; and Advise to live in an easy state. |
| Decrease in blood pressure (pulsation) ↓ | Advise to have massage for relieving menstruation pain; and Advise about breathing method for improving circulation of blood. | There is no problem. Advise to do exercise positively; and Advise to do stretch exercise for improving circulation of blood. | There is no problem. Advise to do exercise positively, while paying attention to any change in physical condition; and Advise to do stretch exercise for improving circulation of blood. | Advise to do exercise for making relax; Advise about meal for adjusting physical condition for preparation for PMS phase; and Advise about breathing method for improving circulation of blooe. | Advise about proper action and nutrition for making relax; and Advise mentally not to have any excessive effort. |

APPARATUS FOR MEASUREMENT OF WOMAN'S BODY

BACKGROUND OF THE INVENTION

1. Field of the Invention

The present invention relates to an apparatus for measurement of woman's body having capability of informing a woman user of her physical condition indicated by the different phases repeated with a period of one month such as menstruation phase, diet phase, before-and-after ovulation phase, PMS (Premenstrual Syndrome) prevention phase and PMS phase.

2. Prior Art

The woman's physical condition indicated by the different phases repeated with a period of one month is intimately related to the basal body temperature, and it has been well known that the basal body temperature is transferred from low temperature term to high temperature term after passing across the boundary of ovulation day, and then transferred from high temperature term back to low temperature term after passing across the boundary of menstruation start day. In the past, such relation has been utilized in such manner that the progress of the basal body temperature of a woman is measured with a clinical thermometer for women at getting-up time in every morning and manually recorded on a list or a graph for determining the physical condition or the phase of the woman in which she is currently positioned.

The prior art measurement of basal body temperature using the clinical thermometer for women, as described above, is defective in that the measurement is very cumbersome and the greater burden is imposed to a person under test. Even if a person desires to only know the number of days during a menstruation period she must record by herself for complicated calculation of the days.

Furthermore, the previous measurement apparatus for body weight, percent fat, etc. have been designed to only display the measurement result of body weight or percent fat. The previous apparatus could produce no advice information based on the body weight or percent fat in connection with the menstruation period, despite of the intimate relation present therebetween.

SUMMARY OF THE INVENTION

An object of the present invention is to provide an apparatus for measurement of woman's body that can solve the prior art problem as described above, that makes possible for everybody to rapidly and easily know the physical condition indicated by the different phases including PMS (Premenstrual Syndrome) phase repeated with a period of one month, and that can give the advice information to a person under test about any optimum nutritive substance to be ingested and/or any proper action to be taken on that measurement day, based on the physical condition, the percent fat, etc.

According to one aspect of the present invention there is provided an apparatus for measurement of woman's body, comprising: a body parameter input unit; a menstruation date input unit; a physical condition phase estimation unit; and a display unit, wherein said body parameter input unit enters the body parameter of a person under test, said menstruation date input unit enters the date of menstruation of the person under test, said physical condition phase estimation unit estimates the phase of physical condition of the person under test to which the measurement day belongs, based on the date of menstruation of the person under test entered by said menstruation date input unit and the formulas for estimation of phase of body condition, and said display unit, after determining any change in body parameter based on the body parameter entered by said body parameter input unit, displays the advice information effective for the person under test to pay attention in living on that measurement day, based on the change in body parameter determined and on the phase of physical condition of the person under test to which the measurement day belongs and estimated by said physical condition phase estimation unit.

In one embodiment of the present invention said body parameter includes at least one of the body weight, percent fat or body fat mass, blood pressure and pulse rate.

In another embodiment of the present invention said phase of physical condition includes a menstruation phase, a diet phase, a before-and-after ovulation phase, a PMS prevention phase and a PMS phase.

In further embodiment of the present invention said phase of physical condition includes a menstruation phase, a diet phase, a PMS prevention phase and a PMS phase.

In yet further embodiment of the present invention said phase of physical condition includes a menstruation phase, a diet phase and a PMS phase.

In yet further embodiment of the present invention said change in body parameter includes a rate of change in body parameter.

In yet further embodiment of the present invention said advice information includes the information about nutrition to be ingested by the person under test and about action to be conducted by the person under test.

According to another aspect of the present invention there is provided an apparatus for measurement of woman's body, comprising: at least one of a body weight input unit, a body fat input unit for entering body far rate or body fat mass, a blood pressure input unit and a pulse rate input unit; a physical condition estimation unit; and a display unit, wherein said physical condition estimation unit estimates the physical condition on the measurement day, based on the date of menstruation entered and the formulas for estimation of phase of body condition, said display unit displays various kinds of advice information about an action, nutrition and the like optimized to the physical condition on the measurement day, based on at least one of the change in body weight provided by the body weight input unit, the change in percent fat or body fat mass provided by the body fat input unit, the change in blood pressure provided by the blood pressure input unit and the change in pulse rate provided by the pulse rate input unit, as well as based on physical condition estimated.

In one embodiment of the present invention said physical condition is at least one of a menstruation phase, a diet phase, a before-and-after ovulation phase, a PMS prevention phase and a PMS phase.

In another embodiment of the present invention said physical condition is at least one of a menstruation phase, a diet phase and a luteal phase.

In further embodiment of the present invention said body weight input unit includes keys for manually entering the body weight value.

In yet further embodiment of the present invention said body weight input unit is a body weight meter.

In yet further embodiment of the present invention said body fat input unit includes keys for manually entering percent fat or body fat mass.

In yet further embodiment of the present invention said body fat input unit is a body fat meter.

In yet further embodiment of the present invention said blood pressure input unit includes keys for manually entering blood pressure value.

In yet further embodiment of the present invention said blood pressure input unit is a blood pressure meter.

In yet further embodiment of the present invention said pulse rate input unit includes keys for manually entering pulse rate.

In yet further embodiment of the present invention said pulse rate input unit is a pulse rate meter.

In yet further embodiment of the present invention said display unit includes an LCD element that displays at least one of body weight, percent fat, body fat mass, blood pressure and pulse rate, and a plurality of LED elements that display the physical condition of a woman.

In yet further embodiment of the present invention said display unit includes a display area of compact size on which at least one of body weight, percent fat, body fat mass, blood pressure and pulse rate; as well as the measurement day, position of the measurement day relative to the menstruation day, the number of days elapsed since the menstruation day up to the measurement day, the number of days during the previous menstruation period and the name of physical condition are displayed.

In yet further embodiment of the present invention said display unit includes a display area of compact size on which a graph representing at least one of the change in body weight, change in percent fat, change in body fat mass, change in blood pressure and change in pulse rate during a menstruation period; as well as the measurement day, position of the measurement day relative to the menstruation day, the number of days elapsed since the menstruation day up to the measurement day, and the number of days during the previous menstruation period are displayed.

BRIEF DESCRIPTION OF THE DRAWINGS

The present invention will be described in more detail with reference to the accompanying drawings, in which:

FIG. 7 is a view illustrating one example of display on the display unit;

FIG. 8 is a view illustrating another example of display on the display unit;

FIG. 9 is a view illustrating further example of display on the display unit;

FIG. 11 is a view illustrating another example of a display unit formed by an LCD element and a plurality of LED elements.

FIG. 12 is an external view of an apparatus for measurement of woman's body according to a second embodiment of the present invention;

FIG. 17 is an external view of an apparatus for measurement of woman's body according to a fourth embodiment of the present invention;

FIG. 19 is a view illustrating another example of calculation formulas for determining the physical condition;

FIG. 20 is a view illustrating further example of calculation formulas for determining the physical condition; and FIG. 21 is a view illustrating another example of advice information according to blood pressure (or pulse rate) and the physical condition.

DESCRIPTION OF THE PREFERRED EMBODIMENT

Figure 1:
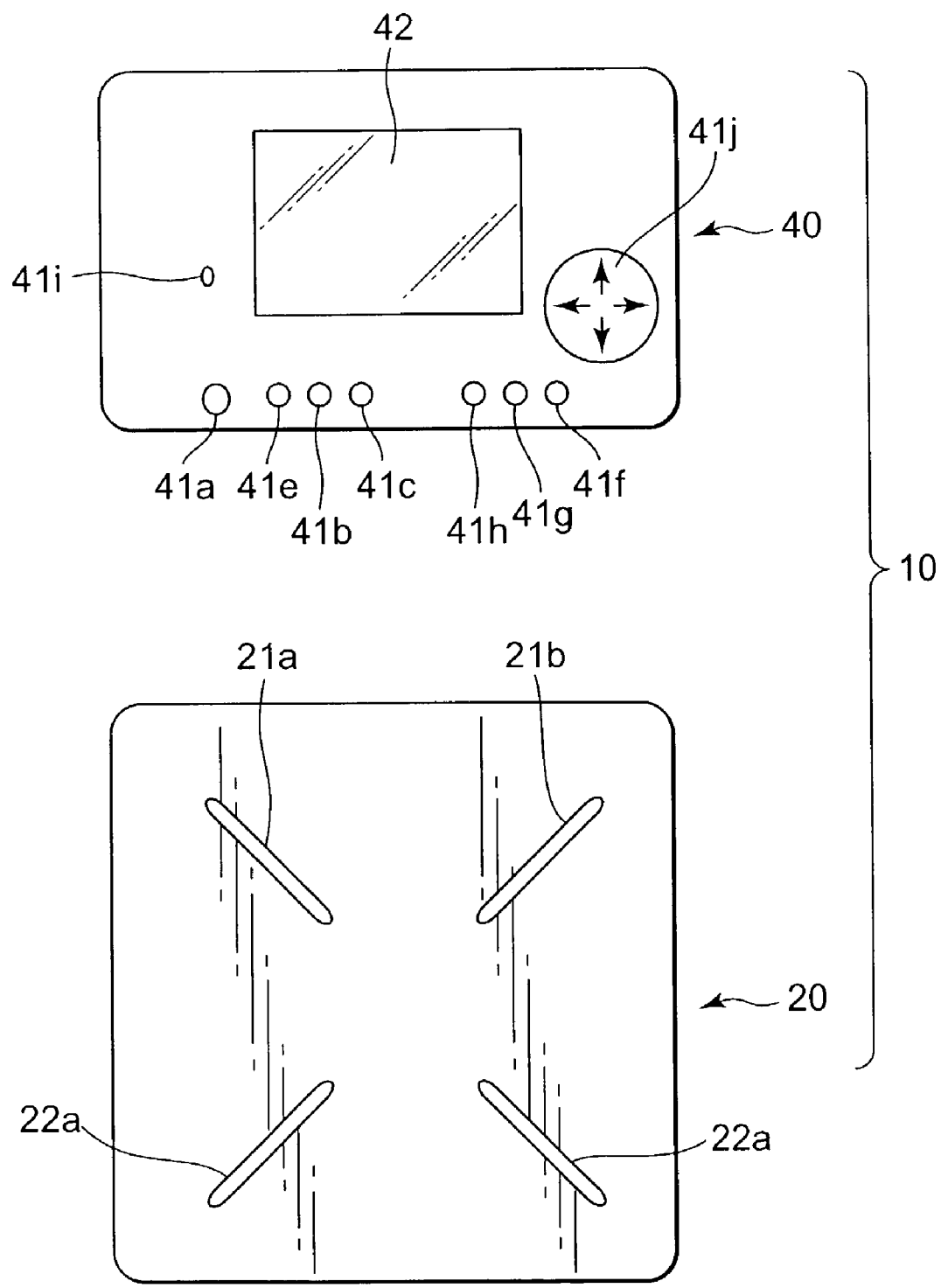
FIG. 1 is an external view of an apparatus for measurement of woman's body according to one embodiment of the present invention.

FIG. 1 is an external view of an apparatus for measurement of woman's body according to one embodiment of the present invention. As shown in FIG. 1, the apparatus for measurement of woman's body 10 comprises a bioelectrical impedance meter 20 with a weight meter included therein, and a control box 40 connected to the bioelectrical impedance meter 20 through the wireless communication using infrared ray, electromagnetic wave, etc.

In this embodiment the bioelectrical impedance meter 20 is connected to the control box 40 via the wireless communication using infrared ray, electromagnetic wave, etc., as described above. However, they may be connected to each other via a typical electrical cable.

Arranged on the top surface of the bioelectrical impedance meter 20 are constant current supplying electrodes 21a, 21b and voltage measurement electrodes 22a, 22b. Mounted on the front surface of the control box 40 are a group of operation keys such as a power key 41a, a measurement key 41b, a record key 41c, a menstruation key 41e, a determination key 41f, a selection key 41g, a cancel key 41h, a reset key 41i and a direction key 41j. In addition, a display unit 42 is also mounted on the front surface of the control box 40. As can be seen in FIG. 1, the direction key 41j consists of "→" key, "←" key, "↑"key and "↓" key.

Figure 2:
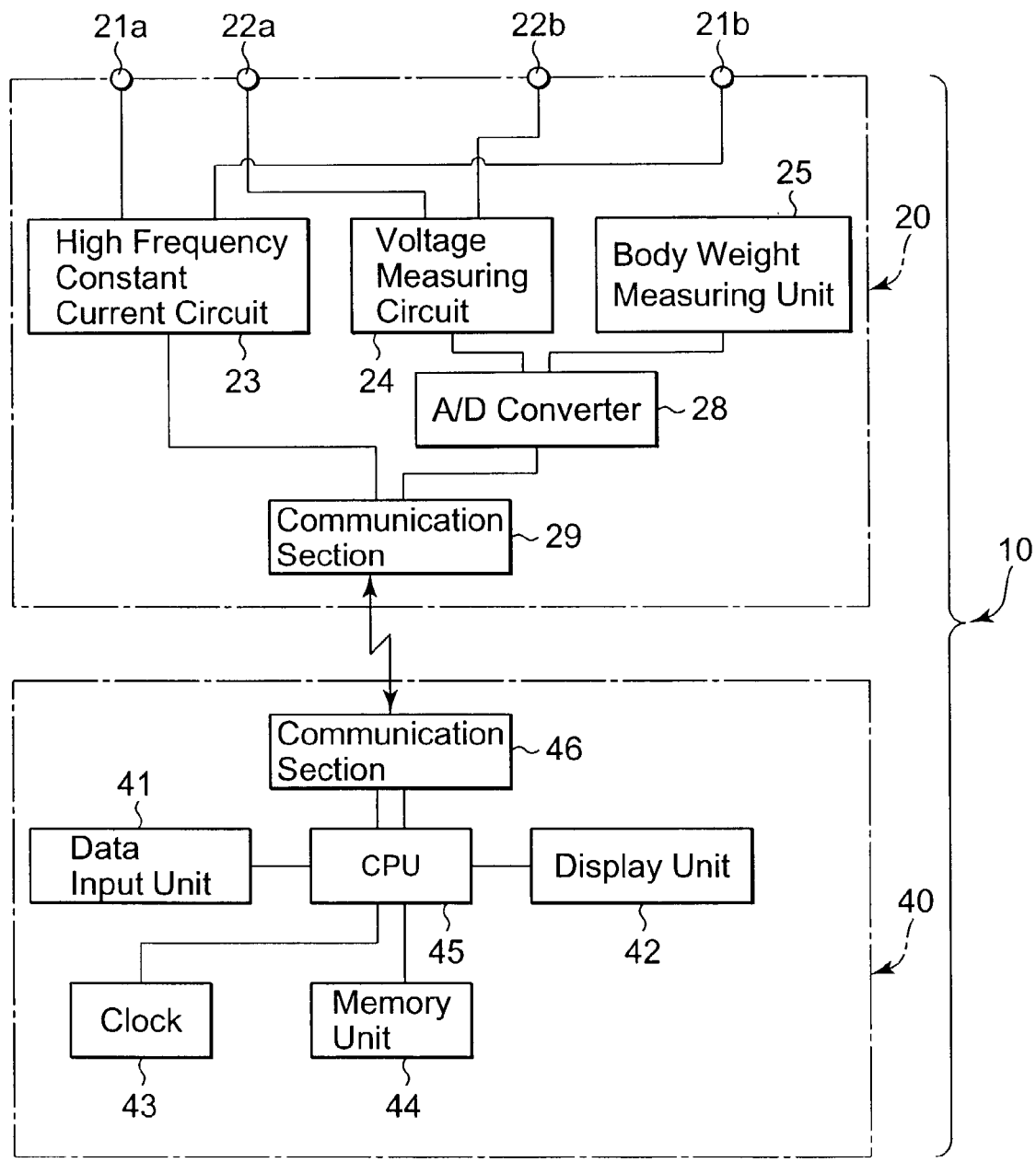
FIG. 2 is a block diagram illustrating functional elements of the apparatus for measurement of woman's body, as shown in FIG. 1.
Figure 3:
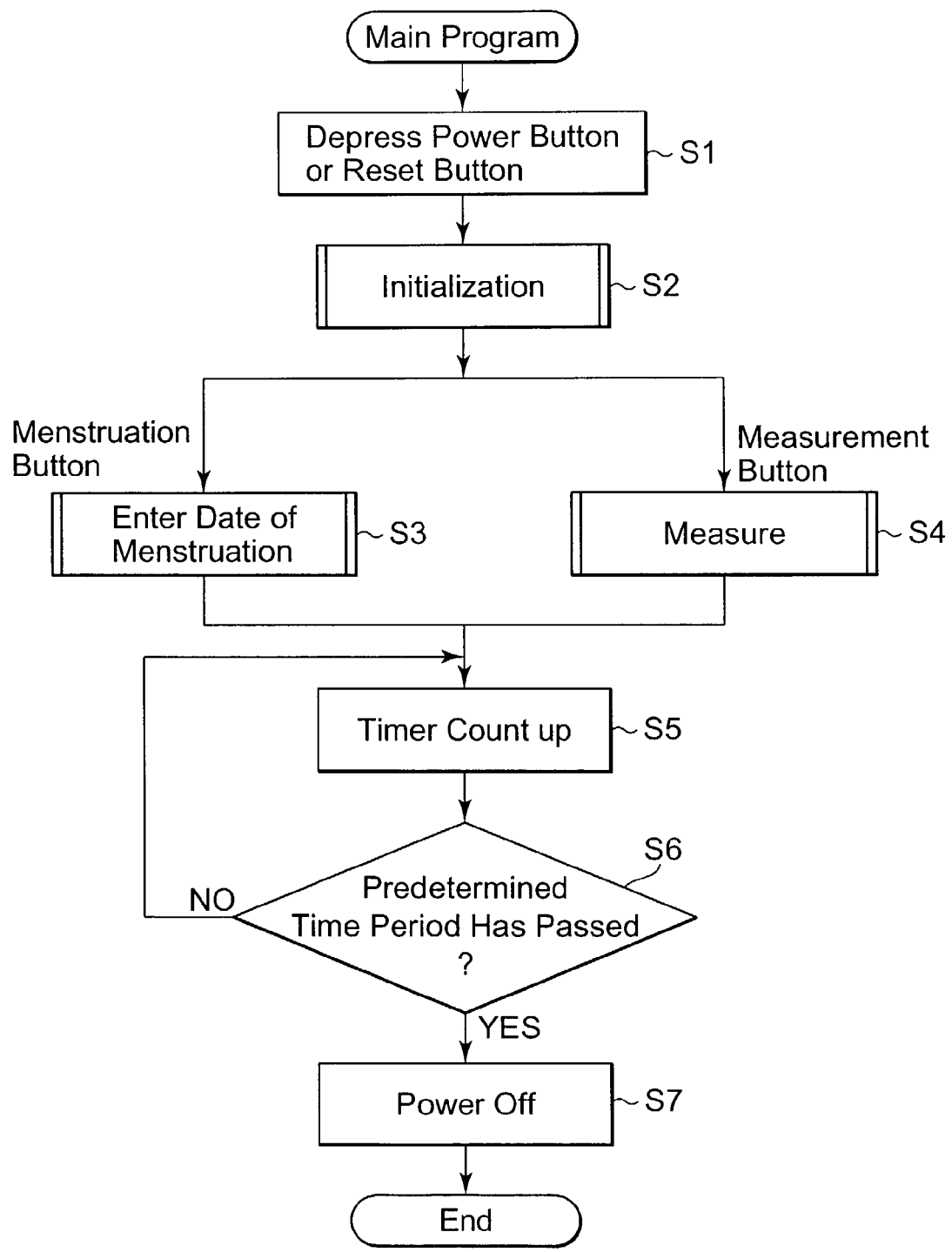
FIG. 3 is a main flow chart illustrating a procedure for giving advice information to a person under test, based on the physical condition of the person and the measurement result according to the present invention.

FIG. 2 is a block diagram illustrating functional elements of the apparatus for measurement of woman's body, as shown in FIG. 1. As shown in FIG. 2, the bioelectrical impedance meter 20 with a weight meter includes constant current supplying electrodes 21a, 21b, a high-frequency constant current circuit 23 for producing a weak high-frequency constant current fed to the constant current supplying electrodes 21a, 21b, voltage measurement electrodes 22a, 22b, a voltage measurement circuit 24 for measuring the voltage across the voltage measurement electrodes 22a, 22b, a body weight measuring unit 25 for measuring the body weight of a person under test, an A/D converter 28 for A/D converting the measured voltage and body weight, and a wireless communication section 29.

The control box 40 includes a data input unit 41 having a group of operation keys 41a to 41j for entering a measurement start command, a menstruation phase data, etc., a display unit 42 for displaying the measured percent fat, body fat mass, body weight, etc., and the determined physical condition, etc., a clock unit 43 for determining the date and time of measurement, and a memory unit 44 for storing the measured percent fat, body fat mass, the determined date and time, etc. The control box 40 further includes a CPU 45 for evaluating the physical condition of a woman repeated substantially for a period of one month and for determining the corresponding advice information, based on the menstruation phase data entered by the input unit 41 and the measured percent fat, body fat mass, body weight, etc. The CPU 45 further controls storage of various data to the memory unit 44 and display of various data on the display unit 42. In addition, a wireless communication section 46 is included in the control box 40.

In this embodiment the functional elements are grouped to be separately included in the bioelectrical impedance meter 20 and the control box 40. However, the present invention is not limited to such configuration. For example, the CPU 45 may be included in the bioelectrical impedance meter 20, not in the control box 40. Furthermore, the bioelectrical impedance meter 20 may be integral with the control box 40.

An operation of the apparatus for measurement of woman's body according to the embodiment as above will now be described in more detail.

FIGS. 3 to 6 are flow charts illustrating the operation of the apparatus for measurement of woman's body according to the present invention. First of all, the main program for operation of the apparatus will be described with reference to FIG. 3. In step S1 a person under test depresses a power key 41a to turn ON the apparatus for measurement of woman's body 10. In step S2 the initialization is performed. The process of initialization will be described later in more detail.

After depressing a menstruation key 41e or a measurement key 41b the program proceeds to step S3 or S4 respectively.

In step S3 the date of menstruation is entered. The process will be described later in detail. In step S4 the measurement is performed. In particular the body weight and the bioelectrical impedance of a person under test is measured and the result is displayed, as described later in detail.

In step 5 an auto-power off timer is counted up. The timer is reset upon power up or by the key operation. In step 6 a check is made to determine whether the predetermined time period has been passed. If not, the program returns to step S5. In step S7 the power is turned OFF.

Figure 4:
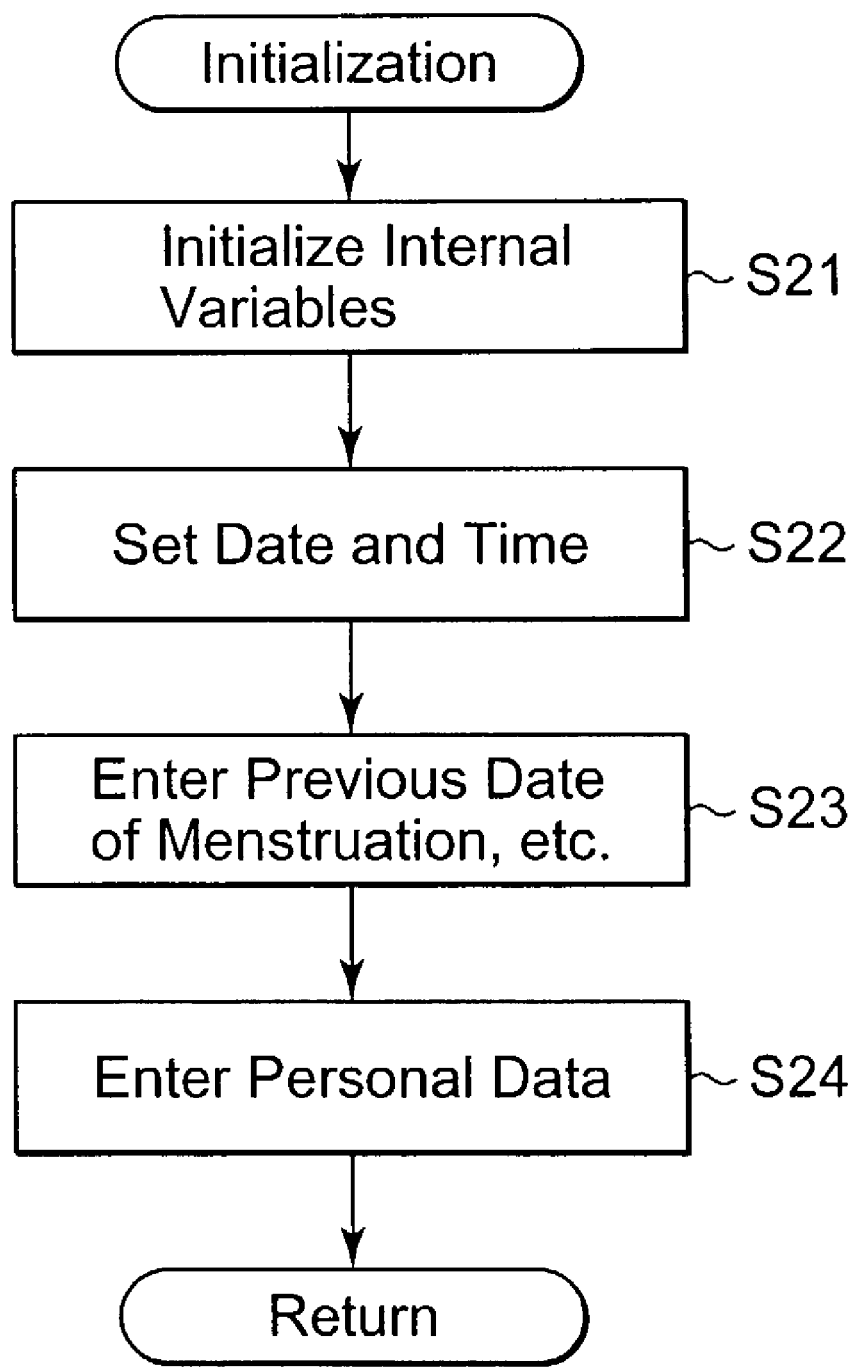
FIG. 4 is a flow chart illustrating the procedure of initialization.

Next, the process of initialization (step S2) will be described in detail with reference to FIG. 4. The initialization is performed only when the power key is depressed for the first time or the reset key is depressed. The determination of whether the power key is depressed for the first time is made in any commonly known method. For example, a variable called "an initialization flag" is provided, and it is set when the initialization is performed. Then, the flag is tested at the first step in which the initialization is to be performed. If it is found that the flag has been set then no further initialization is performed.

In step S21 the internal variables are initialized. In step S22 the inside clock is set at the current date and time. In step S23 the date of previous menstruation and the number of days during the menstruation period are entered if the person under test knows them. In step S24 the personal body information such as sex, height, age, etc., is entered. The apparatus 10 is originally designed for use with a woman, but it may be used with a man if the sex is set to "man" to measure the percent fat, body fat mass, etc. for the man.

Figure 5:
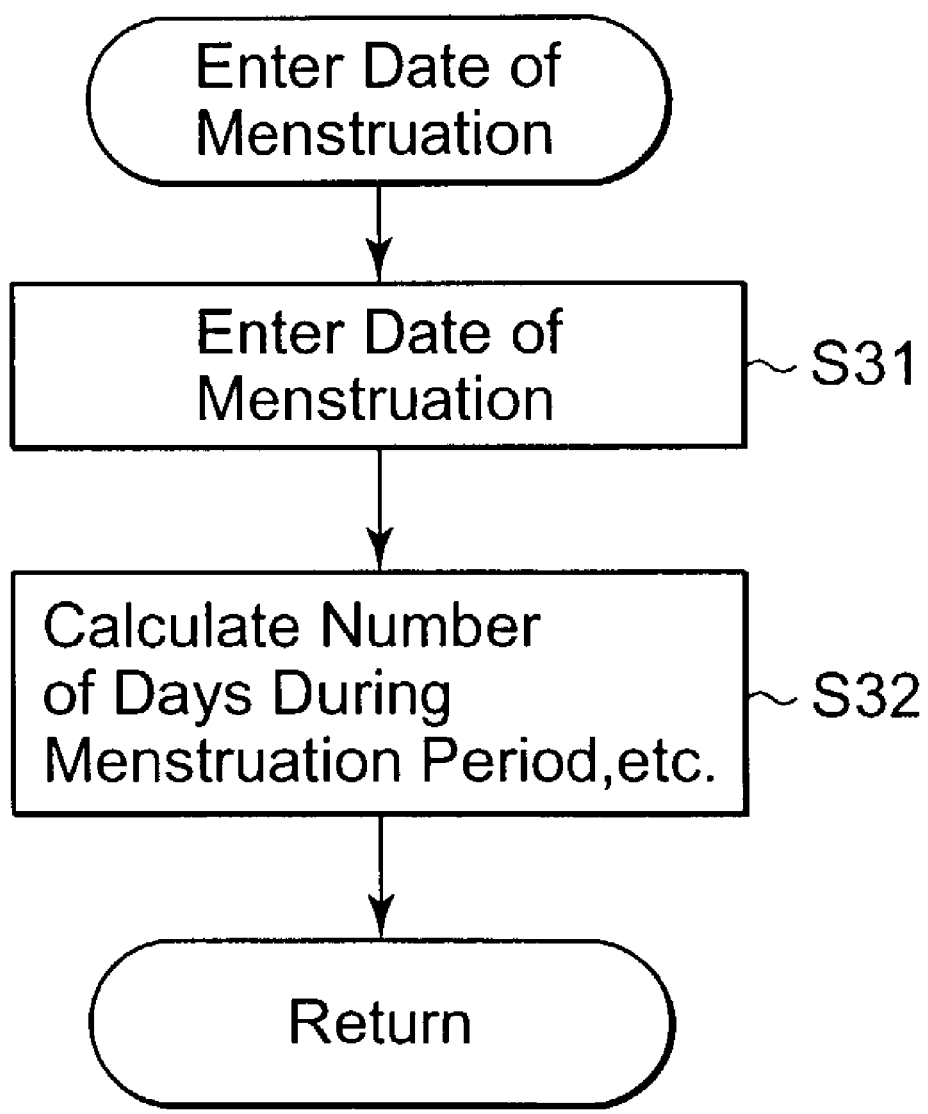
FIG. 5 is a flow chart illustrating the procedure of entering the date of menstruation.

Then, the process of entering the date of menstruation (step S3) will be described in detail with reference to FIG. 5. In step S31 the date of menstruation is entered. In step S32 the number of days during the menstruation period, the average number of days during the menstruation period, the maximum number of days during the menstruation period and the minimum number of days during the menstruation period are calculated, based on the date of menstruation just entered and the date of previous menstruation stored.

Figure 6:
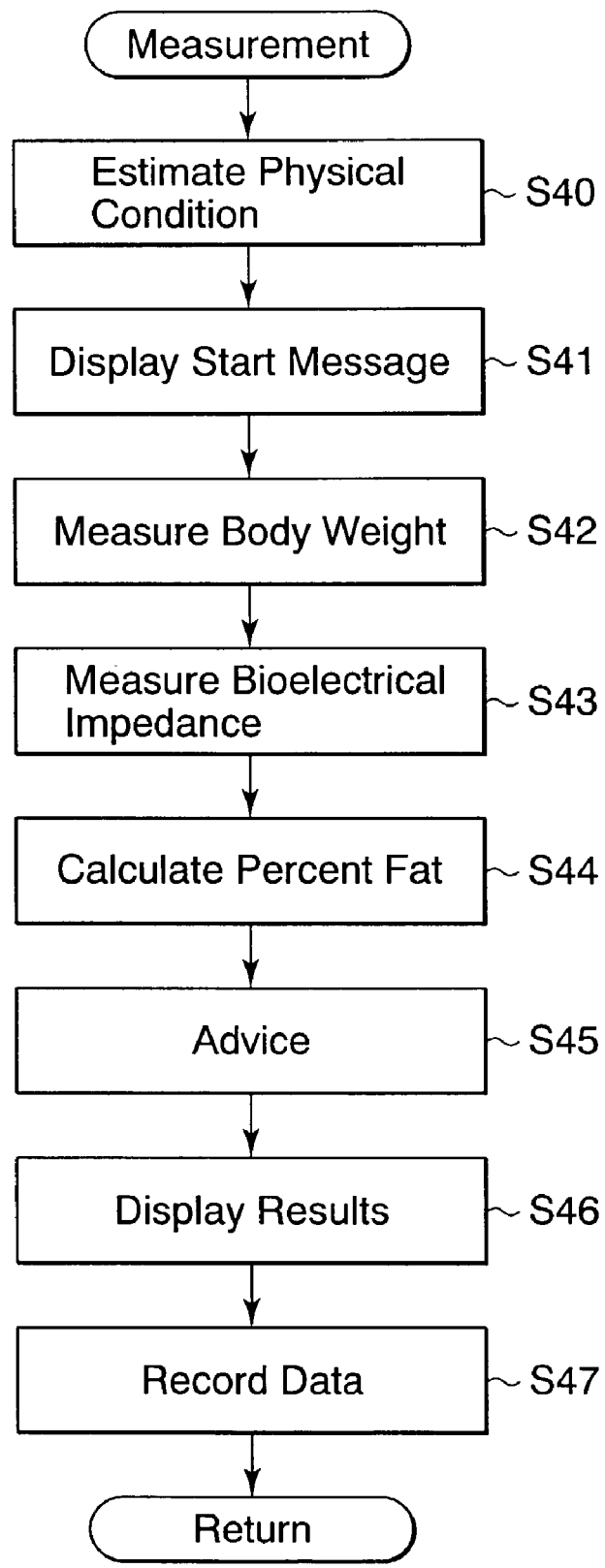
FIG. 6 is a flow chart illustrating the procedure of measurement.

Next, the process of measurement (step S4) will be described in detail with reference to FIG. 6. In step S40 the CPU 25 estimates the phase of physical condition. The date of menstruation entered at step S23 in FIG. 4 or at step S31 in FIG. 5 is considered as the start date of menstruation. Initially the number of days elapsed since the date of previous menstruation is calculated. If the number of days elapsed exceeds the minimum number of days during the menstruation period calculated at step S32 in FIG. 5 then a message is displayed on the display unit 42, informing that "the menstruation day becomes soon. When the menstruation starts, depress the menstruation key and enter the date of menstruation". If the menstruation starts on the measurement day or even if the menstruation already started before the measurement day, but the measurement has not yet been done, then the menstruation key is depressed and the date of menstruation is entered, as shown at step S3 in FIG. 3. Thereafter, the measurement key is depressed once again for conducting the measurement process.

Then, by using the equations for estimating the phase of physical condition, as shown in Table I, below, the first date and the final date of menstruation is estimated and a check is made to determine whether the measurement day belongs to the menstruation phase. If not, the estimation and evaluation process continues to be performed through the diet phase, before-and-after ovulation phase, PMS prevention phase and PMS phase until the phase to which the measurement day belongs is found. Each of phases other than the menstruation phase has two or more types of equations; the top is an equation using the average number of days during the menstruation period; the middle is an equation using the minimum number of days during the menstruation period; and the bottom is an equation using the maximum and minimum number of days during the menstruation period. Which of the equations is used may be determined by the trial-and-error method. When the top equation is used it may be possible that the measurement day belongs to both diet phase and before-and-after ovulation phase. Therefore, if the measurement day belongs to diet phase then the estimation and evaluation process should be done also for before-and-after ovulation phase. If the measurement day belongs to both phases they are considered as the physical condition on that day. The average number, maximum number and minimum number of days during the menstruation period in the equations are those that are calculated at step S32 in FIG. 5.

TABLE I

<Estimation of length of each phase in case where menstruation period is divided into five phases>

| | |
|---|---|
| (1) Menstruation Phase | = 1 ~a |
| (2) Diet Phase (Follicular Phase) | =(a + 1)~{Average number of days during the period −(14+b)} ;or =(a+1)~{Minimum number of days during the period −(14+b)} |
| (3) Before-and-After Ovulation Phase (Ovulation Phase) | ={Average number of days during the period−(14+b−1)−2} ~Average number of days during the period−(14+b−1)+2} ;or ={Minimum number of days during the period−(14+b−1)} −{Minimum number of days during the period−(14+b−1)} ;or ={Maximum number of days during the period−(14+b−1)} −Maximum number of days during the period−(14+b−1)} |
| (4) PMS Prevention Phase (First Half of Luteal Phase) | ={Average number of days during the period−(14+b−1)+ 2+1}~{Average number of days during the period−(7+c)} ;or ={Minimum number of days during the period−(14+b−1) +1)~{Minimum number of days during the period−(7+c)} ;or ={Maximum number of days during the period−(14+b−1) +1)~{Minimum number of days during the period−(7+c)} |
| (5) PMS Phase (Latter Half of Luteal Phase) | ={Average number of days during the period−(7+c)+1} ~{Next menstruation input date−11 ;or =(Minimum number of days during the period −(7+c)+1} ~{Next menstruation input date−1} |

Notes:
"a" means the length of menstruation phase, typically four days;
"b" means an adjustment interval for before-and-after ovulation phase, typically three days; and
"c" means an adjustment interval for PMS phase, typically 0 day.

Table II, below, shows the phases of physical condition in case where the menstruation occurs in 28-day period. An interval of four days after starting the menstruation is considered as the menstruation phase. An interval of seven days from the next day is considered as the diet phase. An interval of five days from the next day is considered as the before-and-after ovulation phase. An interval of five days from the next day is considered as the PMS prevention phase. Finally an interval of a week from the next day is considered as the PMS phase. Any change in physical condition for each of the phases is shown in Table II [this figure].

TABLE II

<Example of Main Physical Variation Occurred with Days since Menstruation (28-day period)>

| Technical Terms | | Menstruation Phase | | | | | | | | | | Before and After Ovualtion | | | | | Luteal Phase | | | | | | | | | | | |
|---|---|---|---|---|---|---|---|---|---|---|---|---|---|---|---|---|---|---|---|---|---|---|---|---|---|---|---|---|
| | | | | | Follicular Phase | | | | | | | | | | | | Luteal Phase | | | | | | | | | | | |
| Terms Marked on Measuring Unit | Days | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| | | ①Menstruation Phase | | | | ② Diet Phase | | | | | | | ③Before and After Ovulation | | | | | ④ PMS Prevention Phase | | | | | ⑤PMS Phase | | | | | | |
| Change in Physical Condition | Basal Metabolism | → Decrease with Start of Menstruation | | | | Stable at Lower Level →→→→ Tend to Gradually Increase | | | | | | | Slightly Increase → Increase after Ovulation | | | | | Higher Level | | | | | Higher Level | | | | | | |
| | Condition | Pay attention to cold or anemia; Poor circulation of blood, Stomachache; Stiffness of shoulder of headache Relieving constipation or suffering from diarrhea; Gradually restoring in latter half interval | | | | Swelling gone down; Physically lightened for becoming activity; Rapid recovery in physical power; Good chance for diet; Skin and hair in good condition; Mentally stable. | | | | | | | Changed in physical condition before and after ovulation (Changed in physical condition after ovulation: gradually becoming poor condition or swelling appeared) | | | | | Heavy swelling appeared (tending to increase in body weight); Headache or stomachache; Feel lassitude or sleepy Irritation: desire to have a food containing much salt or sugar; Increase of appetite (Diet should be avoided); Others: various physically and mentally uncomfortable conditions. | | | | | | | | | | |
| | | Do exercise without any strain | | | | | | | | | | | | | | | | Do exercise without any strain | | | | | | | | | | | |

In the embodiment as above the menstruation period is divided into five phases. However, it may be divided into four phases: menstruation phase, diet phase (follicular phase), PMS prevention phase and PMS phase. Or alternatively it may be divided into three phases: menstruation phase, diet phase (follicular phase) and luteal phase. If the period is divided into four phases then the number of days for each phase is calculated using the equations for estimating the phase, as shown in Table III, below. On the other hand, if the period is divided into three phases then it is calculated using the equations in Table IV, below.

TABLE III

<Estimation of length of each phase in case where menstruation period is divided into four phases>

| | |
|---|---|
| (1) Menstruation Phase | =1~a |
| (2) Diet Phase (Follicular Phase) | =(a+1)~{Average number of days during the period −(14+b)+2};or =(a+1)~{Minimum number of days during the period −(14+b)} |
| (3) PMS Prevention Phase (First Half of Luteal Phase) | ={Average number of days during the period −(14+b−1)+2+1} ~{Average number of days during the period −(7+c)} ;or ={Minimum number of days during the period −(14+b−1)+1} −{Minimum number of days during the period −(7+c)} ;or ={Maximum number of days during the period −(14+b−1)+1} ~{minimum number of days during the period −(7+c)} |
| (4) PMS Phase (Latter Half of Luteal Phase) | ={Average number of days during the period −(7+c)+1} ~{Next menstruation input date−1} ;or ={Minimum number of days during the period −(7+c)+ 1} −{Next menstruation input date−1} |

Notes:
"a" means the length of menstruation phase, typically four days;
"b" means an adjustment interval for ovulation day, typically 0 day; and
"c" means an adjustment interval for PMS phase, typically 0 day.

TABLE IV

<Estimation of length of each phase in case where menstruation period is divided into three phases>

| | |
|---|---|
| (1) Menstruation Phase | =1~a |
| (2) Diet Phase (Follicular Phase) | =(a+1)~{Average number of days during the period −(14+b)+2} ;or =(a+1)~{Minimum number of days during the period −(14+b)} |
| (3) PMS Phase (Luteal Phase) | ={Average number of days during the period −(14+b)+2+1} ~{Next menstruation input date −1} ;or ={Minimum number of days during the period −{14+b)+1} ~{Next menstruation input date −1} |

Notes:
"a" means the length of menstruation phase, typically four days; and
"b" means an adjustment interval for ovulation day, typically 0 day.

If the information that one desires to know is that in the phase suitable for the diet or if there is no need to specify the ovulation day then the diet phase may be combined with the before-and-after ovulation phase to consider as the diet phase. In addition, the PMS prevention phase may be combined with the PMS phase to consider as the PMS phase (luteal phase). In this way the menstruation period may be divided into three phases. If the information that one desires to know is of swelling the menstruation period may be divided into four phases.

For a person who has a possibility of greater change in menstruation period, if the period is divided into five phase, the number of days during any one phase may become very small or may become zero, as the case may be, that provides no meaning. Therefore, for such person, it is preferred that the period is divided into four or three phases.

In step S41 a message informing that "mount on the impedance meter" is displayed on the display unit 42 in flashing form. Depressing the cancel key 41h returns the program back to step S2.

In step S42 the person under test mounts on the bioelectrical impedance meter 20 having the weight meter included therein with the bear feet within 30 seconds in such manner that the toes of left and right soles of the person are in contact with the constant current supplying electrodes 21a and 21b, and the heels of left and right soles of the person are in contact with the voltage measurement electrodes 22a and 22b. Then the weight measuring unit 25 detects the load to start measurement of the body weight. In step S43 the weak high-frequncy constant current produced in the high-frequncy constant current circuit 23 is applied to the toes of the person via the constant current supplying electrodes 21a and 21b so that it flows through the lower abdominal region of the person between the both feet. Then the voltage across the voltage measurement electrodes 22a and 22b is measured with the voltage measuring circuit 24 so that a "BI" (bioelectrical impedance) is derived. In step S44 the percent fat and body fat mass are calculated, based on the derived BI. If the apparatus has no weight meter included therein it is possible to enter the body weight by using the direction key 41j and the determination key. The average body weight for men and women are stored in the memory unit so that it is only necessary to increase/decrease the weight value with the direction key 41j and to determine the value with the determination key. If there is no body fat meter provided in the apparatus the relevant value may be entered manually in the same manner.

In step S45 the advice information is selected according to the change in percent fat or body fat mass and the physical condition. Table V, below, shows one example of the advice information. For example, if the change in percent fat is increased over 0.5% and the physical condition is positioned in the menstruation phase then the advice information "about some light stretch exercised to increase the metabolism while relaxing and about action and nutrition for relieving menstruation pain" is selected. Table V shows the advice information according to the percent fat and the physical condition. However, the percent fat may be replaced with the body fat mass, body weigh or pulse rate and/or blood pressure. In such case, of course, the different advice information is used. The pulse rate and blood pressure may be measured with the pulse rate meter and blood pressure meter, respectively. They may be entered manually, as in the case of manual entering of the body weight. The advice information according to the change in body weight and the physical condition is substantially same as that according to the percent fat and the physical condition in Table V. However, in case of percent fat, "no change in percent fat" is defined as any change within ±0.5%, but in case of body weight, "no change in body weight" is defined as any change within ±0.1%.

TABLE V

| | ① Menstruation Phase | ② Diet Phase | ③ Before-and-After Ovulation Phase | ④ PMS Prevention Phase | ⑤ PMS Phase |
|---|---|---|---|---|---|
| Increase in Percent fat ↑ | Advise to do light stretch for increasing metabolism while relaxing; and Advise about proper action and suitable nutrition for relieving menstruation pain. | Advise to do slightly hard aerobics; Advise about meal likely to provide weight reduction; and Instruct to correct one's behavior. | Watch with a jealous eye! Advise about action not to increase body weight, suitable aerobics, and proper nutrition for restoration from fatigue. | Advise to do light aerobics and to take meal for reducing swelling; and Prepare in an easy state for PIVIS phase. | Advise about meal for eliminating or at least relieving swelling; and Make comfortable to eliminate irritation. |
| No change in Percent fat (within ±0.5%) | Make it easy yourself; Advise about breathing method for increasing metabolism and improving circulation of blood; and Advise about proper action for relieving menstruation pain. | Advise to do aerobics for efficiently reducing body weight; and Advise about meal suitable for providing diet effect. | Gradually become difficult to be lean, but make comfortable; Advise to do light aerobics for longer period of time; and Advise about proper nutrition for restoration from fatigue. | Advise to do exercise for eliminating any irritation and to take meal for preparation for PIVIS phase; and Advise about a water intake not to produce swelling in latter time. | Advise about meal and proper action for prevention of swelling; Advise to do exercise for eliminating any irritation; and Advise to live in an easy state. |
| Decrease in Percent fat ↓ | Take a rest; and Advise to have massage, to do exercise and to take meal for relieving menstruation pain. | Swelling is eliminated and body weight is reduced; and Advise to do exercise for tightening, with some muscle training as the central item to maintain the condition. | Advise to do exercise for tightening to maintain the body shape; and The physical condition is gradually becoming poor, so pay attention. | Advise to do exercise for making relax, and Advise about meal for adjusting physical condition for preparation for PMS phase. | Advise about proper action and nutrition for relaxing, and Advise mentally not to have any excessive effort. |

Table VI, below, shows another example of advice information according to the change of blood pressure or pulse rate and the physical condition. It has been well known in the gynecology that the woman's body has the periodical change in blood composition and heart blood vessel function occurred with the periodical change in sex hormone. Especially in luteral phase, storage of body water occurs, and therefore, there is tendency to pressurize the blood vessel and to increase the blood pressure due to the increased body water. Also in such phase, due to increase in body temperature and metabolism, the pulse rate also tends to increase. If such increase in blood pressure and pulse rate becomes excessive then it may adversely affects the PMS symptom such as headache, fatigue, languor, etc. If there is rapid increase in blood pressure found in such phase that the blood pressure is inherently unlikely to increase then it is expected that it may have relation to some disease. Accordingly it is possible to prompt the person to pay attention. In case where the menstruation period is divided into three or four phases the advice information can be displayed in the same manner as the case where it is divided into five phases.

TABLE VI

| | | | | | |
|---|---|---|---|---|---|
| Increase in blood pressure (pulsation) ↑ | After menstruation the blood pressure (pulsation) will be decreased, but pay attention not to further increase. Save salt as much as possible and keep quiet. When suffering from heavy headache or stomachache, take a rest without any strain. | Any increase in blood pressure (pulsation), if any, in this phase may be a symptom of any disease. Pay attention to save salt. If you feel poor physical condition go to see a doctor for advice. | Give a comment that there may cause big change in physical condition in this phase, and advise to save salt and to adjust the physical condition. | Because of possibility that the blood pressure (pulsation) is further increased after entering PMS phase, pay attention to save salt, to take a lot of vegetable and to adjust the physical condition in advance. | In this phase the blood pressure (pulsation) is likely to be increased, so save salt as much as possible and keep quiet. When suffering from heavy headache or stomachache, take a rest without any strain. (Give an advice about a meal for prevention of swelling.) |
| No change in blood pressure (pulsation) | Make it easy on yourself; Advise to have massage for relieving menstruation pain; and Advise about breathing method for improving circulation of blood. | There is no problem. Advise to do exercise positively. | There is no problem. Advise to do exercise positively, while paying attention to any change in physical condition. | Advise to do exercise for eliminating any stress. Advise about water and salt intake not to produce any swelling. | Advise about proper meal and action to prevent any swelling; Advise to do exercise for eliminating any stress; and Advise to live in an easy state. |
| Decrease in blood pressure (pulsation) ↓ | Advise to have massage for relieving menstruation pain; and Advise about breathing method for improving circulation of blood. | There is no problem. Advise to do exercise positively; and Advise to do stretch exercise for improving circulation of blood. | There is no problem. Advise to do exercise positively, while paying attention to any change in physical condition; and Advise to do stretch | Advise to do exercise for making relax; Advise about meal for adjusting physical condition for preparation for PIVIS phase; and | Advise about proper action and nutrition for making relax; and Advise mentally not to have any excessive effort. |

TABLE VI-continued

| | | exercise for improving circulation of blood. | Advise about breathing method for improving circulation of blood. | |
|---|---|---|---|---|
| ① Menstruation Phase | ② Diet Phase | ③ Before-and-After Ovulation Phase | ④ PMS Prevention Phase | ⑤ PMS Phase |

In step S45 a check is made to determine whether there is any rapid change in body weight occurred. It has been known that the proper weight reduction rate is 2~3% of the body weight before weight reduction for the interval of one month. The rate of change in body weight is defined by the following equation:

Rate of change=(weight value on measurement day−average value for previous three days)÷(average value for previous three days)×100

For example, assuming that the weight values on the measurement day, one day before, two day before and three day before are 50.5 kg, 49.7 kg, 49.2 kg, 50.3 kg, respectively, the rate of change in body weight equals 1.6%. If no measurement was done on any one of the previous three days then the average value for remaining two days is used as the average for previous three days. Furthermore, if the measurement was done on only one of the previous three days then the weight value for that day is used as the average for previous three days. If the body weight is increased due to disordered meal such as excessive eat and drink it is preferable to calculate the rate of change relative to the previous day in order for the person to restore the previous body weight as soon as possible. However, such method could not be performed if no measurement was done. Therefore, in order to handle such case, the rate of change in body weight is derived, based on the average for previous three days.

Next, description is made to what percentage is defined as the rapid rate of change in body weight. According to the probability statistics method the rate of change not less than ±1.5 standard deviation can not be occurred in the usual case. The measurement of body weight was done with certain population and the rate of change at standard deviation of 1.5 was calculated, which resulted in the rate of 1.4%. Accordingly the rate of change not greater than −1.4% and not less than 1.4% is defined as the rapid rate of change.

In the above description the rate of change in body weight has been described, but the rapid rate of change is also determined in the same manner for the percent fat, body fat mass, blood pressure and pulse rate.

In step 46 the measurement result is displayed. FIG. 7 shows one example of display on the display unit 42. The body weight and the percent fat are displayed on an upper half of the compact size display area. In addition, the number of days elapsed since the previous menstruation and the number of days during previous menstruation period are displayed on a lower half of the display area. The number of days during previous menstruation period may be one during the last time menstruation period or during the menstruation period of two times before. Alternatively it may be replaced with either one of the average, minimum or maximum number of days during the menstruation period. The name of phase of physical condition is displayed at the bottom of the display area. In this example the message "in PMS phase" is displayed. If the measurement day belongs to two phases they are considered as the physical condition on that day. Because of all the necessary information displayed on the compact size display area the person can readily understand all the matter.

FIG. 8 shows another example of display. In this example the advice information about the nutrition and action suitable for the physical condition is displayed. For example, Chinese medicine or herb (or aroma therapy) suitable for the physical condition may be displayed. FIG. 9 shows further example of display in which a graph of body weight within the menstruation period, a position information of the measurement day relative to the date of previous menstruation, the number of days elapsed since the date of previous menstruation and the number of days during the previous menstruation period are displayed on the compact size display area. The number of days during the previous menstruation period may be one during the last time menstruation period or during the menstruation period of two times before. Alternatively it may be replaced with either one of the average, minimum or maximum number of days during the menstruation period. According to such display format the person under test can visually understand the change in body weight in view of a period of one month. The graph may show the percent fat, body fat mass, pulse rate or blood pressure, instead of body weight.

Figure 10:
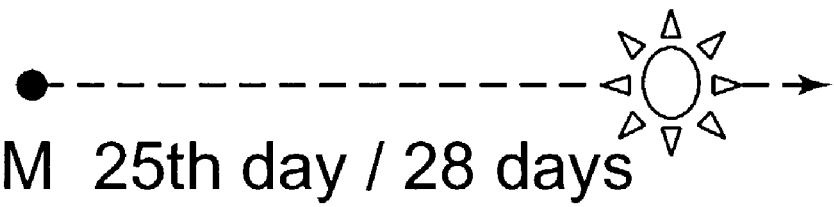
FIG. 10 is a view illustrating one example of a display unit formed by an LCD element and a plurality of LED elements.

FIG. 10 shows the display unit 42 formed by an LCD (liquid crystal display) element and a plurality of LED (light emitting diode) elements. The LCD element is positioned at upper left of the display unit for displaying only body weight and percent fat. Under the LCD element the LED element each marked by a circle (O) are positioned on a line representing the basal body temperature. One of the LED elements of which position corresponds to the phase of physical condition on that measurement day is operated to flash. In this example it is apparent that the person under test is positioned at the before-and-after ovulation phase. The LED elements, if used, can reduce the cost of the display unit.

FIG. 11 shows the LED elements positioned on a straight line.

Such display format is very useful for understanding the change in physical condition in view of the menstruation period and for improving the physical condition.

In step S47, after elapsing the predetermined time interval, a message "depress the record key for data storage" is displayed on the display unit 42. When depressing the record key 41c the measurement result of "BI", body weight, etc. is stored in the memory unit 44. Then the procedure returns to the main program.

Figure 15:
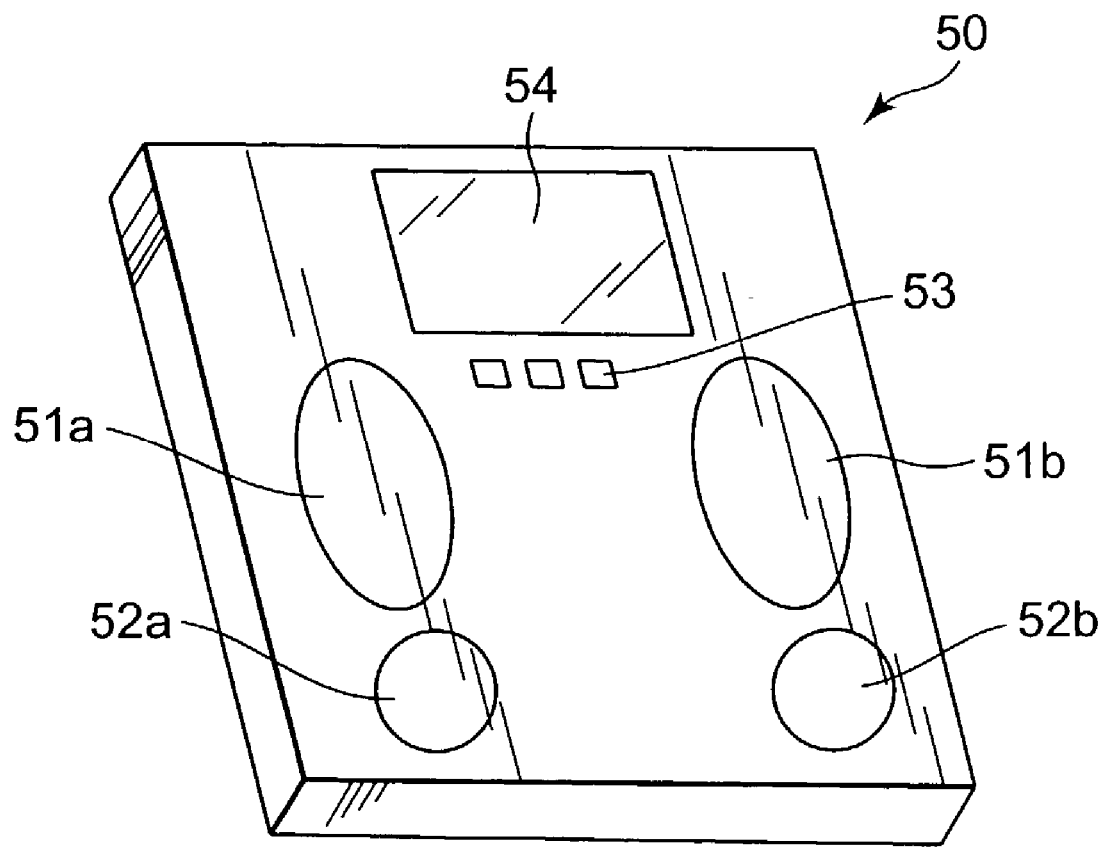
FIG. 15 is an external view of an apparatus for measurement of woman's body according to the fifth embodiment of the present invention.
Figure 16A:
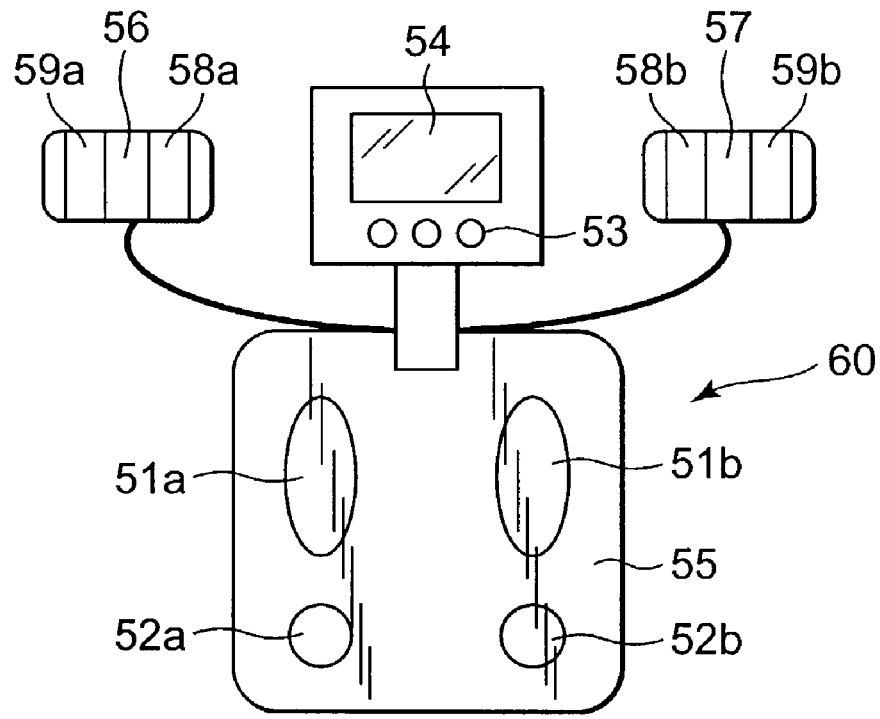
FIG. 16 is an external view of an apparatus for measurement of woman's body according to a third embodiment of the present invention.
Figure 16B:
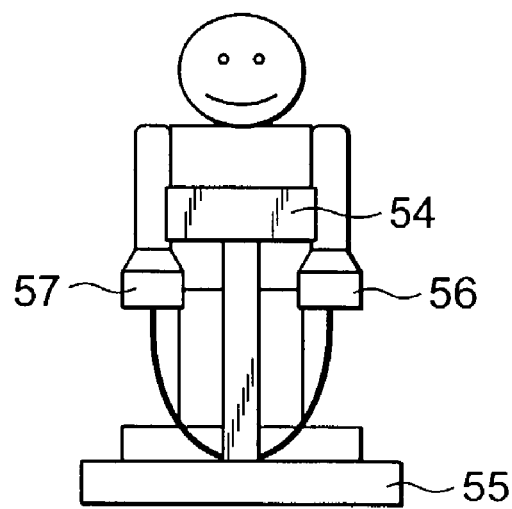
Figure 18:
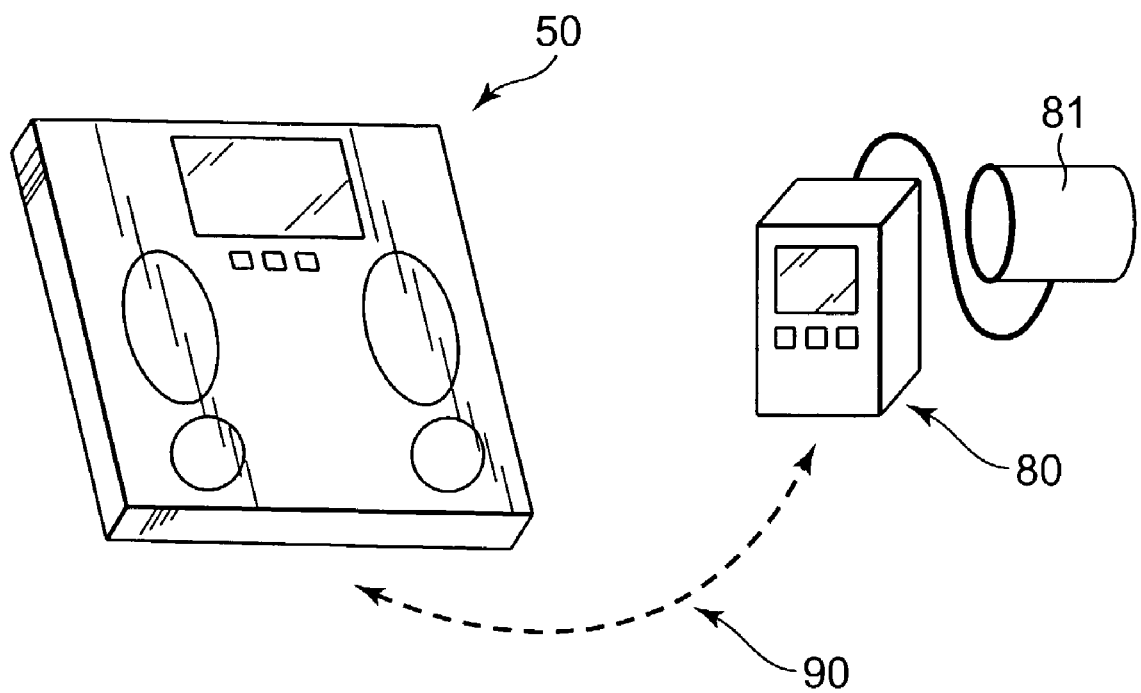
FIG. 18 is an external view of an apparatus for measurement of woman's body according to a fifth embodiment of the present invention.

Now, other embodiments of the present invention will be described. FIG. 15 is a perspective external view of an apparatus for measurement of woman's body according to a second embodiment of the present invention. This apparatus 50 as shown in FIG. 15 is different from the apparatus 10 of the first embodiment as shown in FIG. 1 in that a bioelectrical impedance meter with a weight meter included therein is not separated from, but is integrated with a control box. Constant current supplying electrodes 51a, 51b, voltage measurement electrodes 52a, 52b, operation keys 53 and a display unit 54 are mounted on an upper surface of the apparatus 50.

Now, other embodiments of the present invention will be described. FIG. 12 is a perspective external view of an apparatus for measurement of woman's body according to a second embodiment of the present invention. This apparatus 50 as shown in FIG. 12 is different from the apparatus 10 of the first embodiment as shown in FIG. 1 in that a bioelectrical impedance meter with a weight meter included therein is not separated from, but is integrated with a control box. Constant current supplying electrodes 51a, 51b, voltage measurement electrodes 52a, 52b, operation keys 53 and a display unit 54 are mounted on an upper surface of the apparatus 50.

Figure 13:
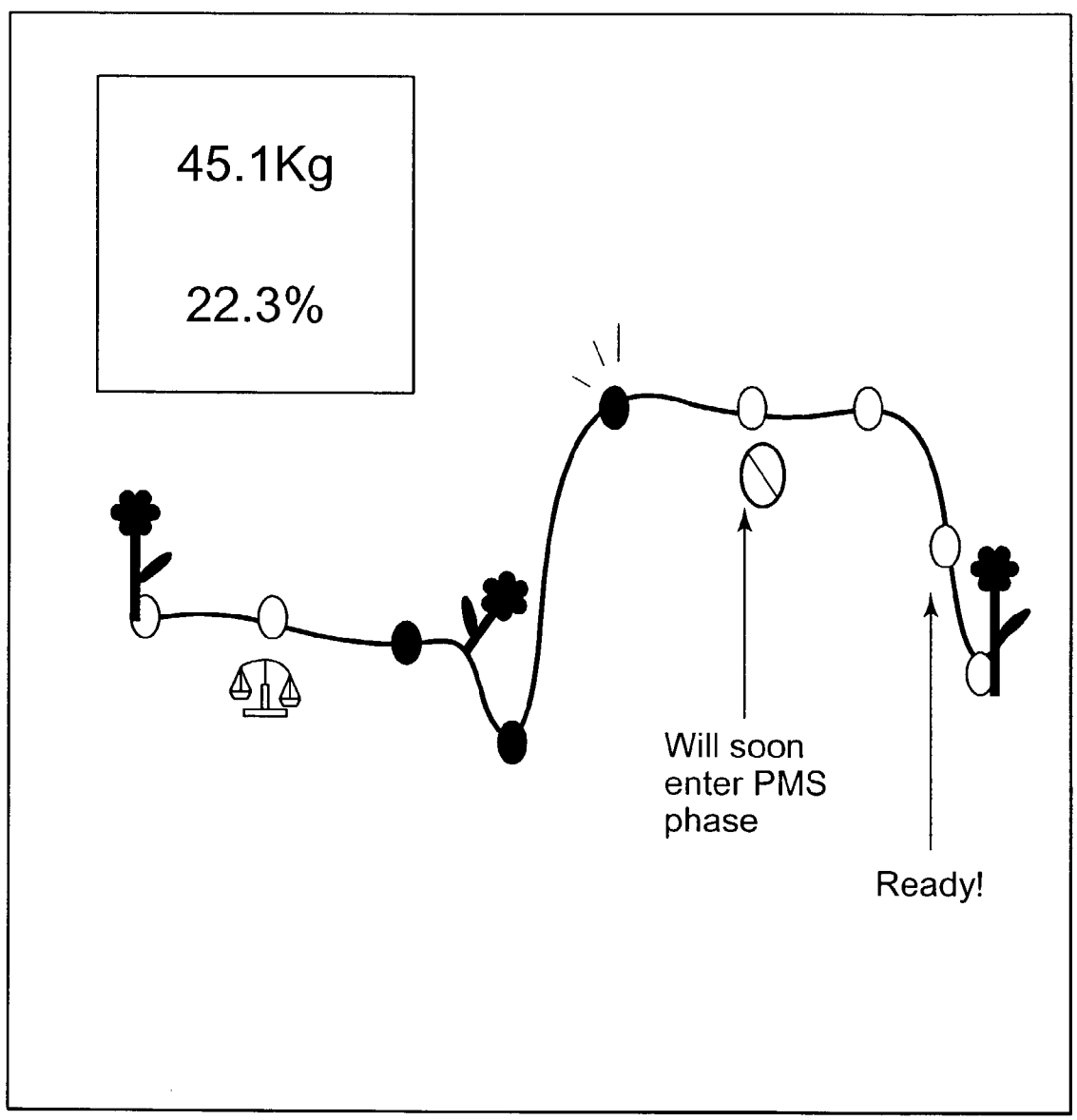
FIGS. 13A and 13B are external views of an apparatus for measurement of woman's body according to a third embodiment of the present invention.

FIGS. 13A and 13B are external views of an apparatus for measurement of a woman's body according to a third embodiment of the present invention. This apparatus is different from that of the second embodiment as shown in FIG. 12 in that the hand electrodes 56, 57 are additionally provided. Not only the "BI" between both feet, but also the "BI" between both hands or between hands and feet can, of course, be measured. For the components equivalent to those in the second embodiment the like reference numbers are used in FIGS. 13A and 13B. The left hand electrode 56 is provided with a constant current supplying electrode 58a and a voltage measurement electrode 59a. Similarly, the right hand electrode 57 is provided with a constant current supplying electrode 58b and a voltage measurement electrode 59b.

Figure 14:
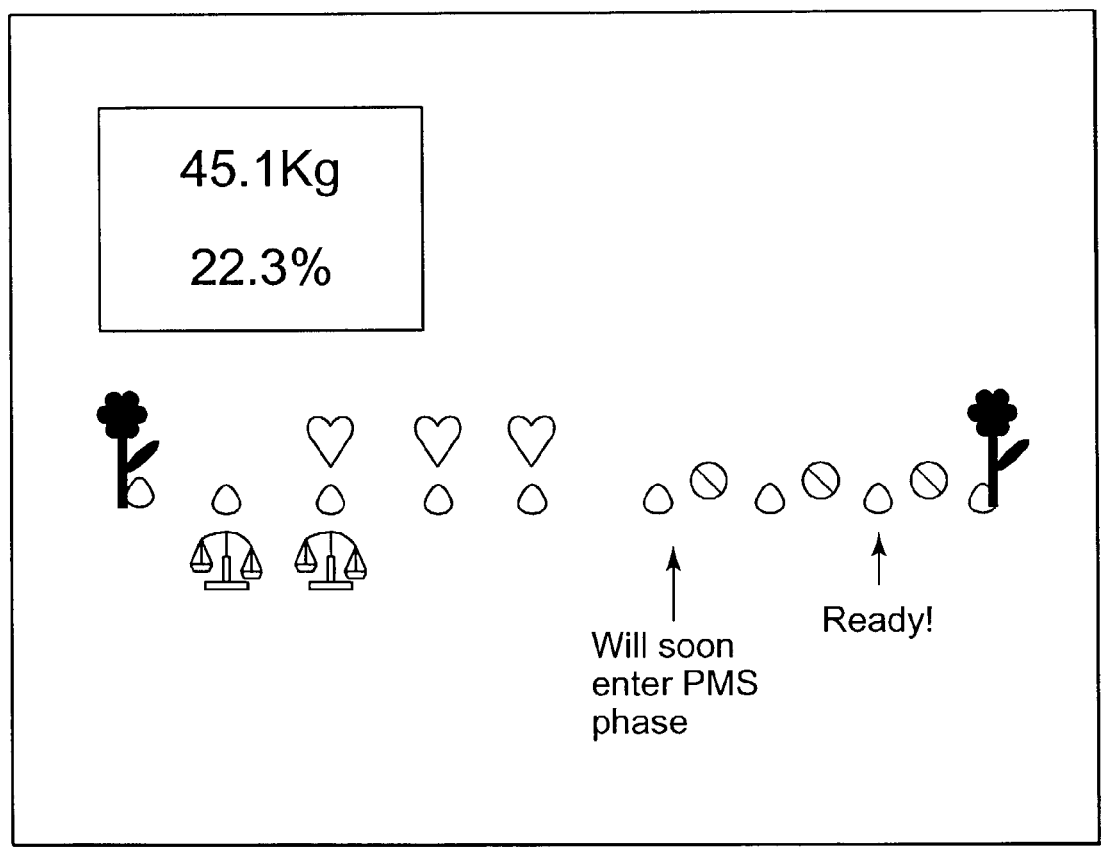
FIG. 14 is an external view of an apparatus for measurement of woman's body according to a fourth embodiment of the present invention.

FIG. 14 is an external view of an apparatus for measurement of woman's body according to a fourth embodiment of the present invention. This apparatus 70 is designed to measure the "BI" between both hands, which is in contrast to the apparatus of FIG. 12 wherein it measures the "BI" between both feet. This apparatus 70 includes constant current supplying electrodes 71a, 71b, voltage measurement electrodes 72a, 72b, a measurement key 73a, a menstruation key 73b, an advice information display key 73c, direction keys 73d, 73e and a display unit 74.

Upon measurement a thumb finger of a left hand is made contact with the electrode 71a and a palm of the left hand is made contact with the electrode 72a. In the similar manner a thumb finger of a right hand is made contact with the electrode 71b and a palm of the right hand is made contact with the electrode 72b.

FIG. 15 is an external view of an apparatus for measurement of woman's body according to a fifth embodiment of the present invention. A blood pressure/pulse rate meter 80 is connected to the body measurement apparatus 50 of the second embodiment in FIG. 12 via a cable or wireless communication 90 using an infrared ray, etc. Reference number 81 shows a cuff for a wrist. In this embodiment the advice information not only about body weight and percent fat, but also about blood pressure and pulse rate can be produced.

The apparatus may be designed not only for one person, but also for plural persons by such configuration that the measurement data for plural persons can be stored and a selection key is provided for selecting any one of the persons.

In this specification the measurement of percent fat has been described as performed by an impedance method, by way of an example, but the sebum thickness method using a caliper or other method using ultrasonic wave or near infrared ray may be used.

In the first to fifth embodiments as above the body weight, percent fat, body fat mass, blood pressure and pulse rate have been described as measured by each measurement unit. However, an alternative configuration may be used wherein the key switches such as the direction key 41j, the determination key 41f, etc., are operated for manual input of those values. In such case a construction similar to the control box of the first embodiment may be adopted, and therefore, the apparatus of the present invention can be provided in the form of portable type apparatus such as a calculator, etc.

It is apparent from the foregoing that an apparatus for measurement of woman's body according to the present invention provides the advice information most suitable for body condition of a person under test on that day, based on the measurement results of body weight, percent fat, body fat mass, etc. and the physical condition occurred with a period of menstruation, which can make the person under test readily understood her own physical condition associated with a period of menstruation and can relieve any uncomfortable feeling due to menstruation or poor physical condition prior to menstruation.

Because of automatic calculation and storage of the number of days during the period, that is specific to each person under test, without any manual calculation needed, management of own menstruation period can easily be done and the recorded data is highly effective for consulting the obstetrics and gynecology.

Furthermore, because of combination of the actual measurement result with the menstruation period for displaying the most effective advice message, unlike the simple management of the number of days, the person under test can be given the advice information according to the true physical condition for relieving any poor physical condition associated with menstruation. The measurement is performed simultaneously with the body weight measurement so that the person under test is imposed substantially no burden, unlike any prior art measurement for menstruation. Therefore, it is very easy for everybody to continue the measurement with the apparatus of the present invention for assisting in understanding and managing the own physical condition for longer period of time.

What is claimed is:

1. An apparatus for measurement of woman's body, comprising:

at least one of a body fat input unit for entering body fat rate or body fat mass, a blood pressure input unit and a pulse rate input unit;

a physical condition estimation unit; and a display unit, wherein said physical condition estimation unit estimates the physical condition on the measurement day, based on formulas for estimation of phase of body condition, said display unit displays various kinds of advice information about an action, or about nutrition optimized to the physical condition on the measurement day, based on at least one of the change in percent fat or body fat mass provided by the body fat input unit, the change in blood pressure provided by the blood pressure input unit and the change in pulse rate provided by the pulse rate input unit, as well as based on physical condition estimated; and said pulse rate input unit includes keys for manually entering pulse rate.

2. An apparatus for measurement of woman's body according to claim 1 in which said physical condition is at least one of a menstruation phase, a diet phase, a before-and-after ovulation phase, a PMS prevention phase and a PMS phase.

3. An apparatus for measurement of woman's body according to claim 1 in which said physical condition is at least one of a menstruation phase, a diet phase and a luteal phase.

4. An apparatus for measurement of woman's body according to claim 1 in which said body fat input unit includes keys for manually entering percent fat or body fat mass.

5. An apparatus for measurement of woman's body according to claim 1 in which said body fat input unit is a body fat meter.

6. An apparatus for measurement of woman's body according to claim 1 in which said blood pressure input unit includes keys for manually entering a blood pressure value.

7. An apparatus for measurement of woman's body according to claim 1 in which said blood pressure input unit is a blood pressure meter.

8. An apparatus for measurement of woman's body according to claim 1 in which said pulse rate input unit is a pulse rate meter.

9. An apparatus for measurement of woman's body according to claim 1 in which said display unit includes an LCD element that displays at least one of body weight, percent fat, body fat mass, blood pressure and pulse rate, and a plurality of LED elements that display the physical condition of a woman.

10. An apparatus for measurement of woman's body according to claim 1 in which said display unit includes a display area of compact size on which at least one of body weight, percent fat, body fat mass, blood pressure and pulse rate; as well as the measurement day, position of the measurement day relative to the menstruation day, the number of days elapsed since the menstruation day up to the measurement day, the number of days during the previous menstruation period and the name of physical condition are displayed.

11. An apparatus for measurement of woman's body according to claim 1 in which said display unit includes a display area of compact size on which a graph representing at least one of the change in body weight, change in percent fat, change in body fat mass, change in blood pressure and change in pulse rate during a menstruation period; as well as the measurement day, position of the measurement day relative to the menstruation day, the number of days elapsed since the menstruation day up to the measurement day, and the number of days during the previous menstruation period are displayed.

12. An apparatus for measurement of woman's body according to claim 1 in which said formulas have at least one of a menstruation period, a length of menstruation phase, an adjustment interval for before-and-after ovulation phase, an adjustment interval for PMS phase, and an adjustment interval for ovulation day as variable.

* * * * *